(12) United States Patent
Mikysa (10) Patent No.: US 6,481,846 B1
(45) Date of Patent: Nov. 19, 2002

(54) EAR AND EYE PROTECTION APPARATUS

(76) Inventor: Erik I. Mikysa, 3601 NW. 70th St., Oklahoma City, OK (US) 73116

( * ) Notice: Subject to any disclaimer, the term of this patent is extended or adjusted under 35 U.S.C. 154(b) by 0 days.

(21) Appl. No.: 09/632,984

(22) Filed: Aug. 4, 2000

(51) Int. Cl.[7] .............................. G02C 1/00; G02C 5/16
(52) U.S. Cl. ........................................ 351/158; 351/114
(58) Field of Search ................................. 351/158, 111, 351/114, 121, 155, 156, 123; 2/209, 10, 452

(56) References Cited

U.S. PATENT DOCUMENTS

| | | | | |
|---|---|---|---|---|
| D207,187 S | | 3/1967 | Gould | D51/1 |
| 4,106,119 A | * | 8/1978 | Taupin | 2/12 |
| 4,511,226 A | | 4/1985 | Freeman | 351/57 |
| 4,621,378 A | | 11/1986 | Hatchman | 2/9 |
| 4,670,911 A | * | 6/1987 | Dunford | 2/209 |
| 4,686,712 A | * | 8/1987 | Spiva | 2/10 |
| 4,930,885 A | | 6/1990 | Laschober | 351/156 |
| 5,268,710 A | | 12/1993 | Anstey | 351/121 |
| 5,278,999 A | | 1/1994 | Brown et al. | 2/209 |
| 5,323,493 A | * | 6/1994 | Ogiba | 2/422 |
| 5,341,516 A | * | 8/1994 | Keim | 2/452 |
| 5,353,071 A | | 10/1994 | Bradshaw | 351/158 |
| 5,386,254 A | | 1/1995 | Kahaney | 351/60 |
| 5,406,340 A | * | 4/1995 | Hoff | 351/156 |
| 5,511,251 A | | 4/1996 | Brakas | 351/116 |
| 5,579,400 A | | 11/1996 | Ballein | 381/183 |
| 5,706,360 A | | 1/1998 | Khandekar | 351/156 |
| 5,818,569 A | | 10/1998 | Berent | 351/156 |
| 5,924,138 A | | 7/1999 | Baisden | 2/209 |
| 5,940,892 A | | 8/1999 | Morgan | 2/430 |
| 6,149,268 A | * | 11/2000 | Hall et al. | 351/158 X |

OTHER PUBLICATIONS

Catalog advertisement from Liftoff, p. 86, date unknown.

* cited by examiner

Primary Examiner—Huy Mai
(74) Attorney, Agent, or Firm—Coats & Bennett, P.L.L.C.

(57) ABSTRACT

A headset and eyewear combination comprises a headset adapted to cover the ears of a user and having a portion of a fastener on the exterior surface of the headset. Eyewear is selectively secured to the exterior portion of the headset with a complimentary portion of the fastener. The eyewear is thereby maintained over the face of the user by means of flexible temples.

12 Claims, 11 Drawing Sheets

EAR AND EYE PROTECTION APPARATUS

FIELD OF THE INVENTION

The present invention relates to combining a device that covers the ears, such as headphones, with some form of eye protection device, such as sunglasses, in such a manner that the invention allows both the ear covering device and the eyewear to be worn simultaneously, while providing full efficaciousness for both devices.

BACKGROUND OF THE INVENTION

Many sorts of individuals wear ear protection devices such as headphones. Construction workers may wear earmuffs to protect themselves from loud machinery noises, which, if not guarded against, could destroy hearing. Likewise, hunters may wear earmuffs to protect their hearing from the loud reports associated with their firearms. Skiers wear earmuffs to protect their ears from the cold. Grounds crewmen at airfields or on aircraft carriers likewise wear earmuffs to protect their hearing from the roar of jet engines as the jets maneuver about the airfield. Pilots and other aviators may likewise wear headphones, albeit for perhaps a different reason. In general, the headsets of aviators double as ear protection and as a communications device. The headphones act as speakers through which the aviators may hear instructions such as from an air traffic control tower or the like. Other professions may also wear headsets. In general, these headsets, whether for protection, communications, or some other desired purpose, come in a number of shapes and sizes. However, it is common for these devices to have a cushion or resilient member, which completely encompasses the ear, forming a seal therearound, and a band, which arches over the head of the wearer, helping hold the set in a desired position.

In addition to headsets, many of these people may also wear some form of eye protection. Construction workers may have safety goggles to prevent debris from getting in their eyes. Hunters wear glasses to protect themselves from ejected shells, vented hot gases, and also as glare protection on sunny days. Skiers wear goggles to keep snow from their eyes and reduce glare from the snow. Likewise, aviators and grounds crewmen may wear sunglasses or prescription glasses in the course of their work. Besides traditional eyewear, aviators may sometimes wear hoods to help them in instrument training sessions. While not eye protection per se, these hoods are eyewear of sorts.

Traditionally, glasses are formed from a lens holding mechanism and a pair of temples that are adapted to slide over the ear of the user. Some temples may curl over and behind the ear, while others may merely extend straight back along the side of the head, resting on the cartilage joining the external ear to the head. If the eyewear has a temple that slides over the ear, and the eyewear is worn with a headset, a number of undesirable things may happen. The seal of the headset around the ear may be broken, thereby allowing ear injuring noise, cold, or other environmental hazards into the headset, defeating its purpose. Also, the temple may be pressed against the side of the head of the wearer, causing discomfort. The pressure of the headset may, over time, deform the temple, such that the eyewear is no longer suitable for wearing.

One solution to these problems is the use of a flexible, head-encircling "temple," coupled to the eyewear such as is sometimes seen on vision-impaired athletes. Thus, an elastic band encircles the head of the wearer, holding the glasses in place during vigorous activity. As a general solution, these devices work fine. However, these devices should be positioned about the head of the wearer prior to donning any headset. Thus, if at some subsequent point, the wearer wishes to remove the eyewear, he or she must doff the headset, remove the eyewear and subsequently re-don the headset. This is a time consuming and annoying process. Alternatively, the individual may not initially need the eyewear, but desire to don it at some later time, such as a pilot not wearing sunglasses until cloud cover has been cleared. In these situations, the headset must be removed, the eyewear put in position, and the headset put back on. Again, this process is annoying, time consuming, and for a busy pilot who may have his hands relatively full flying the plane, perhaps dangerous.

There remains a need for a form of eyewear that is compatible with a headset; that does not require the wearer to remove the headset when donning or doffing the eyewear; and that may be retrofitted to existing headsets without great expense, as these headsets may be relatively expensive, especially in the case of aviators' and hunters' headsets.

SUMMARY OF THE INVENTION

The problems of the prior art are addressed by providing a headset with a part of a fastener available on an outside surface thereof. The fastener mates with a complementary portion of the fastener positioned proximate the terminal end of a flexible temple of the eyewear. Thus, the headset may be positioned properly over the ears of the wearer, and the eyewear may be attached to the headset at a later time without removing the headset.

An alternate embodiment of the invention comprises a kit for retrofitting eyewear to an existing headset. In this embodiment, the eyewear portion remains the same. However, the kit includes the fasteners that may be attached to the headset. In particular, the fasteners may include an adhesive that may be applied to the headset such that a portion of the fastener may be secured to the headset.

The type of fastener may be varied amongst many that exist. In particular, fasteners such as a hook-and-loop fastener, a snap, a button, and the like may be used. Flexible material for the temples may also be varied amongst many acceptable materials. A durable fabric or plastic material may be particularly well suited for the present invention. The eyewear may vary between sunglasses, prescription glasses, prescription sunglasses, protective eyewear without prescription qualities, a training hood, goggles, or the like as needed or desired. The headsets may be varied between earmuffs such as hunters use, earmuffs such as skiers use, headsets that pilots use, protective earwear such as construction workers may use, portable radio headsets, or the like as needed or desired.

An alternate embodiment includes using the eyewear as described on a helmet rather than a set of headphones.

By securing the eyewear to the outside of the headset, the seal created around the ear is maintained. Further, the individual may doff or don the eyewear without having to remove the headset.

DETAILED DESCRIPTION OF THE PREFERRED EMBODIMENT

The present invention solves the problems associated with the prior art by providing eyewear that includes flexible temples. The flexible temples each include a portion of a fastener near the terminal ends thereof for selective attachment to a headset. The headset may have a complementary portion of the fastener. The flexible nature of the temples makes it possible to conform the eyewear to a number of different faces and headsets while preserving the utility of both the headset and eyewear.

Figure 1:
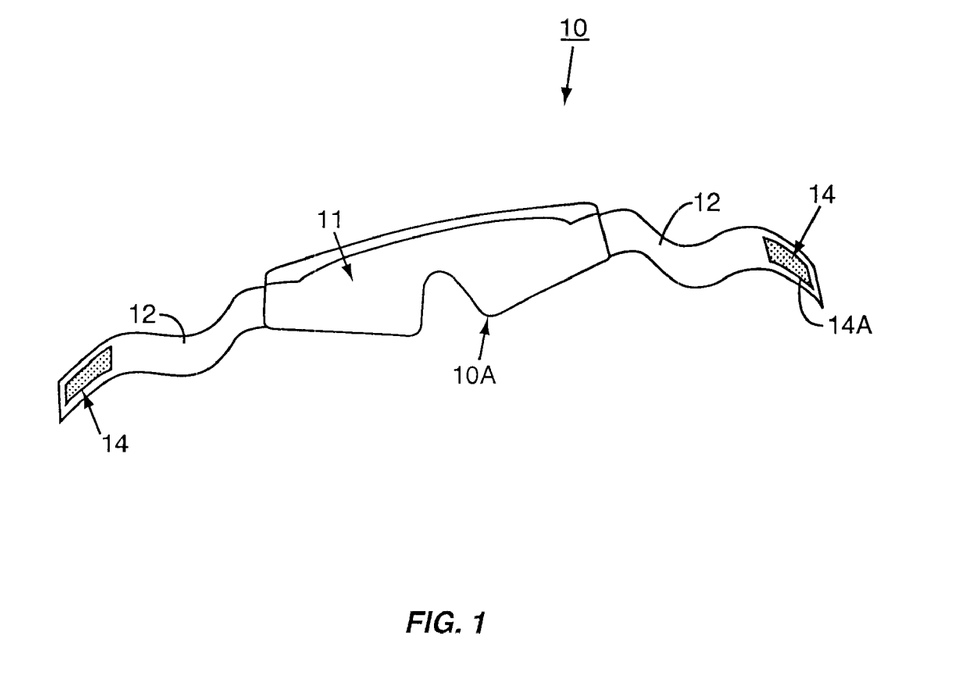
FIG. 1 illustrates a perspective view of an eyewear device adapted for the present invention.

Turning now to the drawings, eyewear 10 is illustrated. In the embodiment of FIG. 1, eyewear 10 takes the form of sunglasses 10A that include lenses 11, temples 12, and fasteners 14. It should be appreciated that sunglasses 10A could equivalently be normal prescription glasses, prescription sunglasses, or the like as needed or desired. As such, lenses 11 may include a tint, a reflective surface, or the like as needed or desired. Temples 12 are made from a flexible material. In particular, temples 12 may be made from an elastic or inelastic material. I.e., the temples 12 may stretch like spandex or be of a generally constant length. Natural or synthetic fibers may be used. Thus, it is possible that the temples 12 may be made from a substantially flexible plastic material. Fastener 14 is discussed in greater detail below, but, for example, fasteners 14A may be one-half of a hook-and-loop fastener such as VELCRO™, and may be positioned proximate the terminal end of temples 12.

Figure 2:
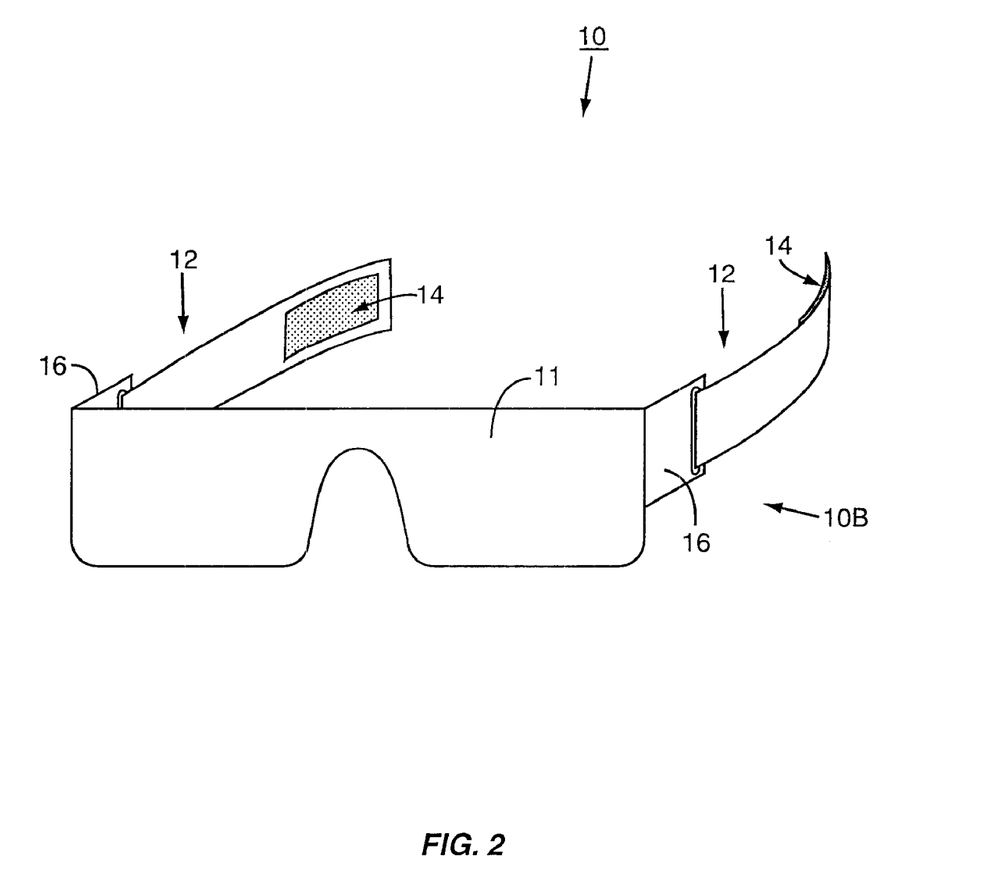
FIG. 2 illustrates a set of protective eyewear adapted for the present invention.

In an alternate embodiment, eyewear 10 may comprise protective goggles 10B as shown in FIG. 2. In this embodiment, temples 12 may further include hinged side protective shields 16 such as may commonly exist on protective eyewear. While it could be argued that protective shields 16 are part of the lenses 11, for the purposes of the present invention, they are defined to be part of the temples 12. It should be appreciated that protective goggles 10B may equivalently be lab goggles, such as are used in chemistry labs, a welder's mask or the like. Protective shields 16 may include slots through which temples 12 are secured.

Figure 3:
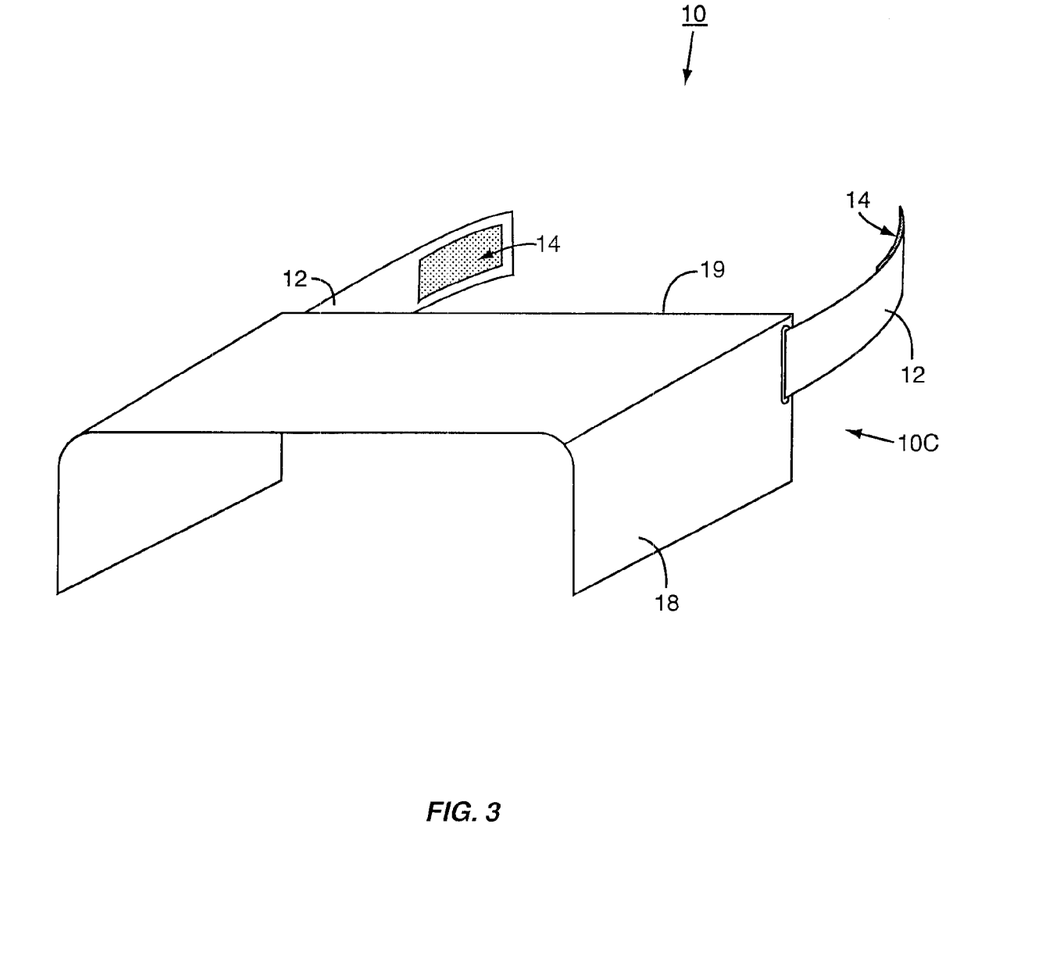
FIG. 3 illustrates a perspective view of a hood adapted for the present invention.

In yet another alternate embodiment, illustrated in FIG. 3, eyewear 10 may be a vision restrictive hood 10C such as are used for Instrument Flight Rule (IFR) training. Hood 10C may include a protective hood 18 and slots at first end 19 thereof such that the temples 12 may be secured thereto. Although not eyewear per se, devices such as the hood 10C are to be construed as falling within the definition of eyewear for the purpose of the present invention.

Figure 4A:
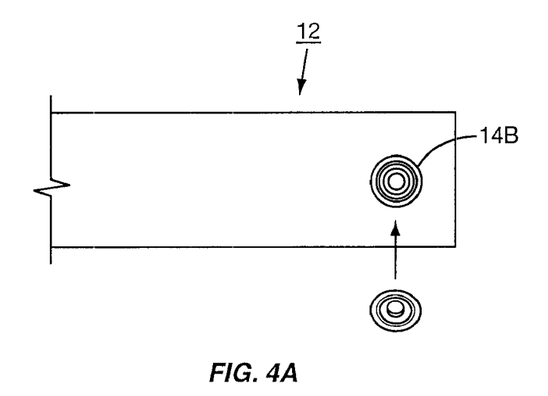
FIGS. 4A–4C illustrate exemplary fasteners such as may be used in the present invention.
Figure 4B:
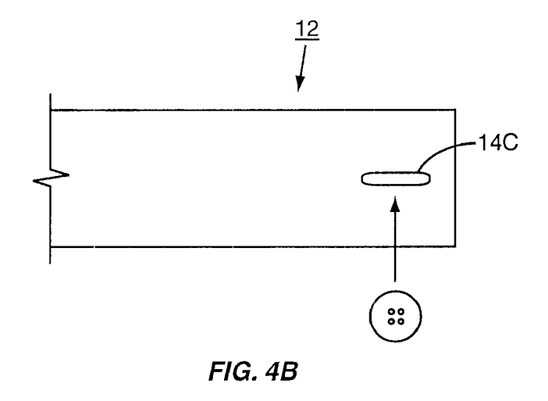
Figure 4C:
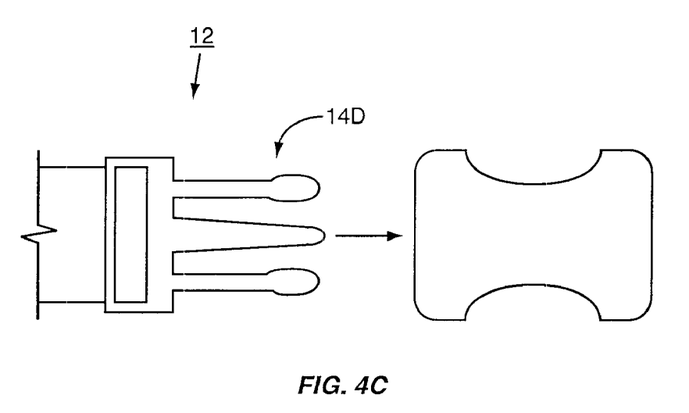
Figure 5A:
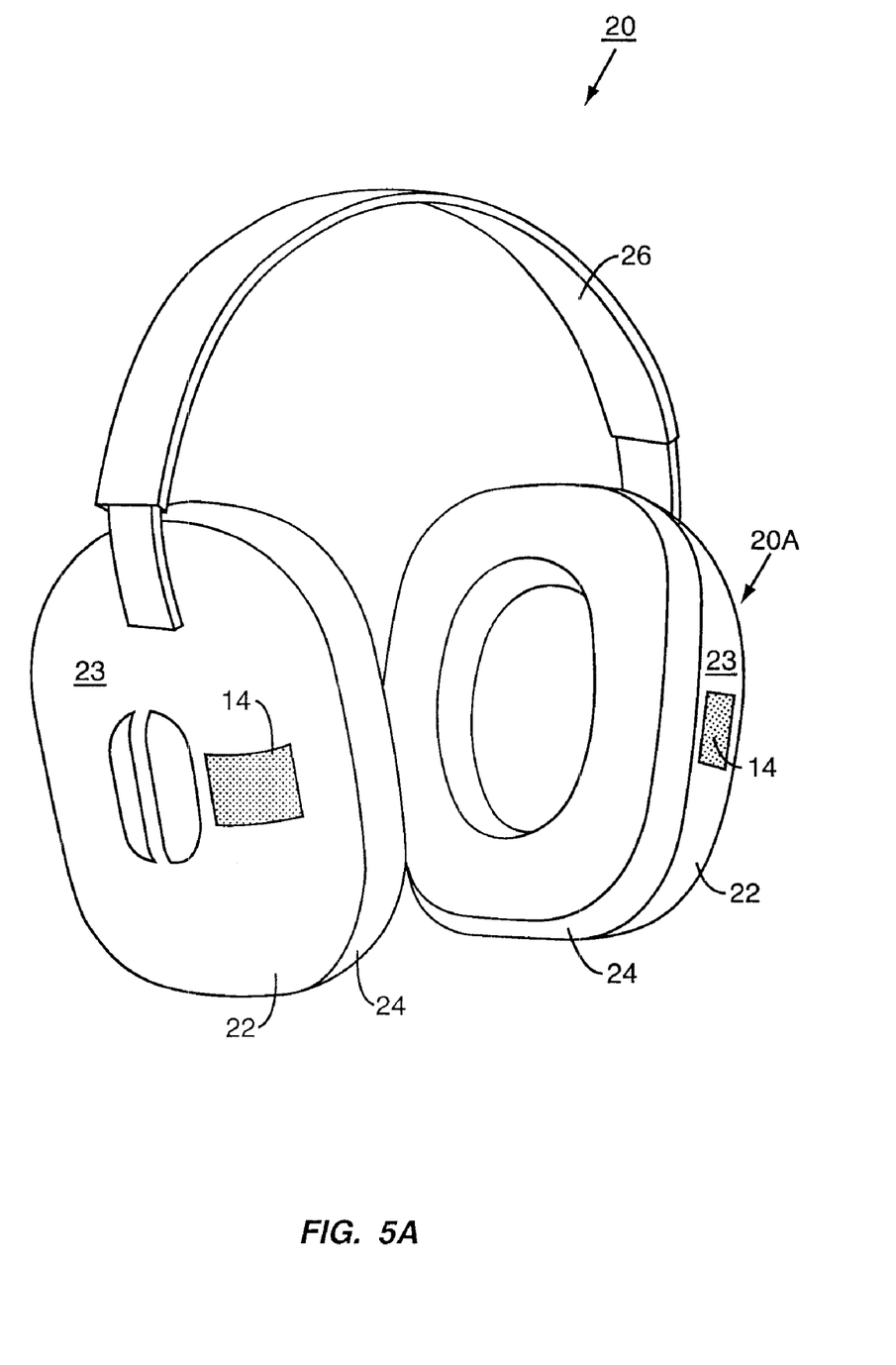
FIGS. 5A–5D illustrate exemplary headsets adapted for the present invention.
Figure 5B:
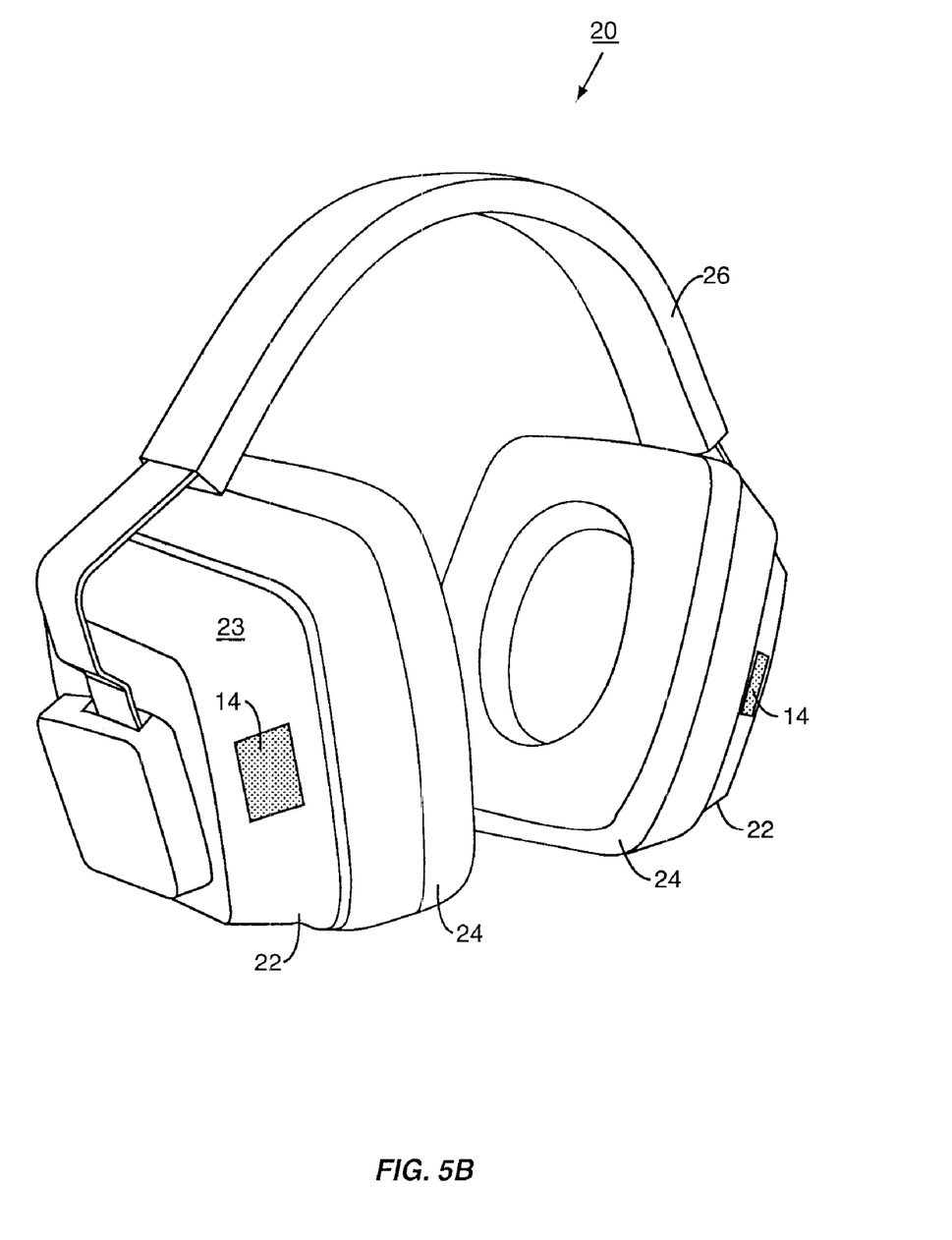
Figure 5C:
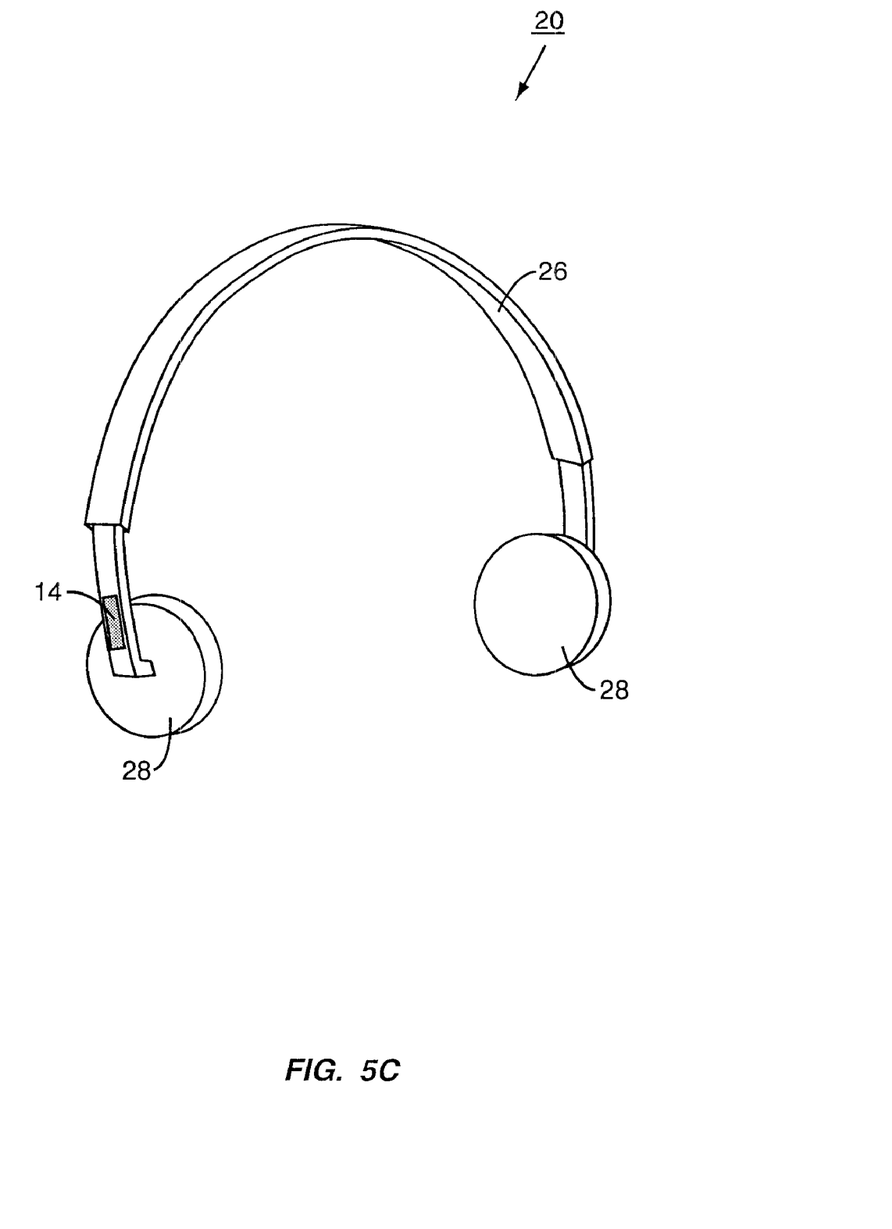

Turning now to FIGS. 4A–4C, a plurality of fasteners 14 are shown therein. In particular, FIG. 4A illustrates a snap-style fastener 14B. FIG. 4B illustrates a button-style fastener 14C wherein the temple 12 includes a slot to receive the button therethrough. FIG. 4C illustrates a clasp-type fastener such as is commonly found on nylon webbing. Other fasteners may equivalently be substituted in the aforementioned embodiments and those mentioned are for illustrative purposes only. It is to be understood that the fastener 14 may include a first member attached to the temple 12, and a second member attached to the headset 20 (FIGS. 5A–5C). When the two members are mated together, the eyewear 10 is securely, but removably (in a nondestructive fashion) attached to the headset 20. In one embodiment, the members provide a positive confirmation when they are attached. By way of example, the snap-style fastener 14B, in FIG. 4A may provide an audible "click" sound when the members are positively connected. Likewise, the button-style fastener 14C allows the user to feel the button positioned through the receiving member of the temple 12. This is important as the temples may often secure the eyewear 10 to the headsets 20 at a point that is not visible to the user.

In addition to the plurality of eyewear 10 and fasteners 14, a plurality of different types of headsets may be used with the present invention. Turning now to FIG. 5A, a headset 20 includes rounded muffs 22 with protective seals 24 and arch 26. Arch 26 is designed to arch over the head of the user to hold the muffs 22 in a desired position. On an exterior surface 23 of muff 22, a complimentary portion of fastener 14 is secured thereto. In FIG. 5A, the other side of a hook-and-loop fastener 14A is illustrated. It should be appreciated that complimentary portions of a snap 14B, a button 14C, or a clasp 14D may be put on exterior surface 23. FIG. 5B illustrates an alternate form of headset including squared off muffs 22, and seals 24.

Yet another alternate embodiment illustrated in FIG. 5C wherein a portable radio headset similar to that used with a SONY WALKMAN™ may be used with the present invention. Arch 26 remains substantially the same with earplugs/speakers 28 used to convey music to the user. Fastener 14 is secured to an external surface on arch 26. Other headsets are also contemplated such as skiers' earmuffs, construction workers' headsets, hunters' headsets with external audio speakers, hands free cellular headsets, and the like.

Figure 5D:
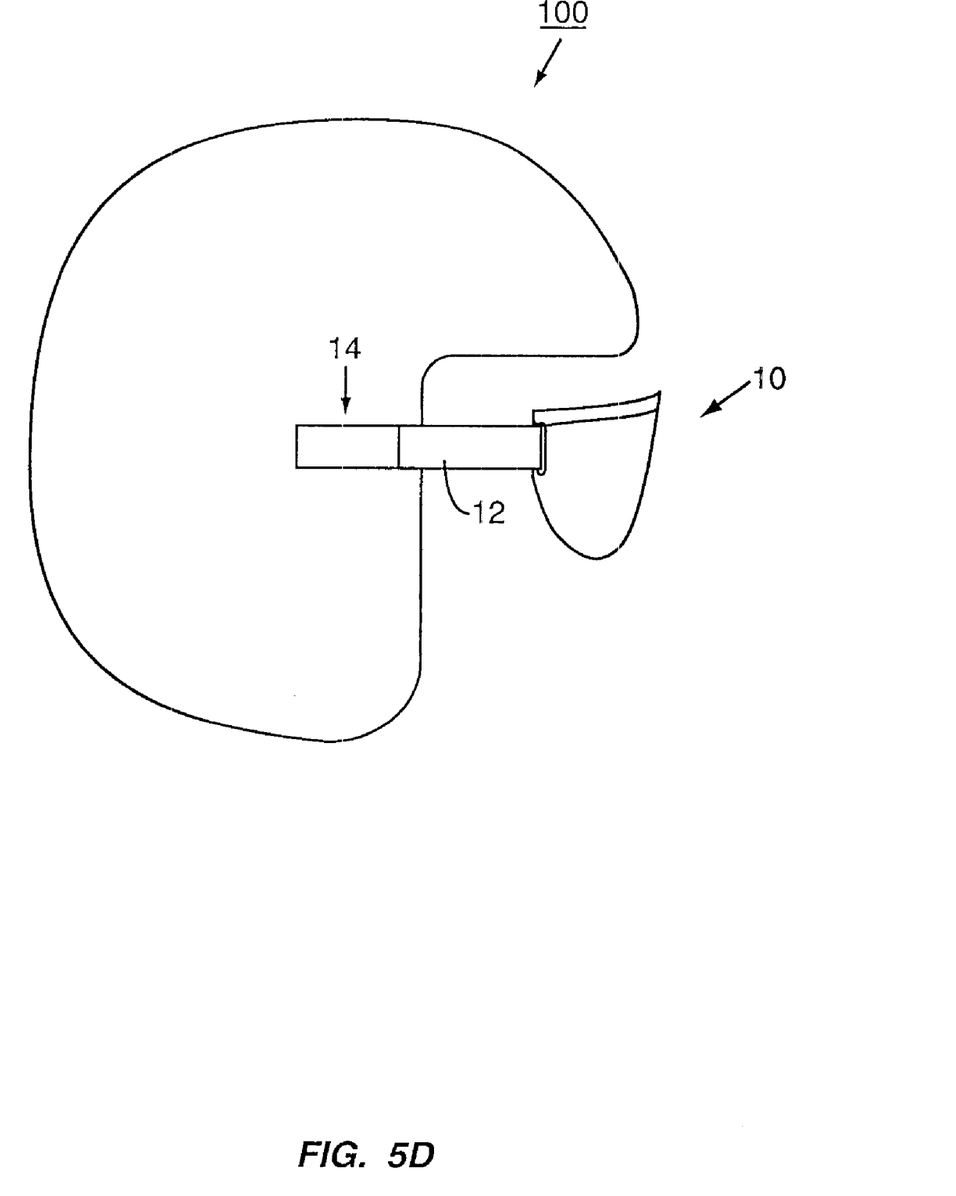

FIG. 5D illustrates eyewear 10 applied to a helmet 100. For the purposes of the present invention, helmet 100 may be considered a headset 20. Helmet 100 may be any of a number of helmets such as are worn by motorcyclists, sport pilots, ultra-light pilots, parachutists, or the like. Any appropriate fastener 14 may be used to secure the temple 12 to the helmet 100.

Figure 6:
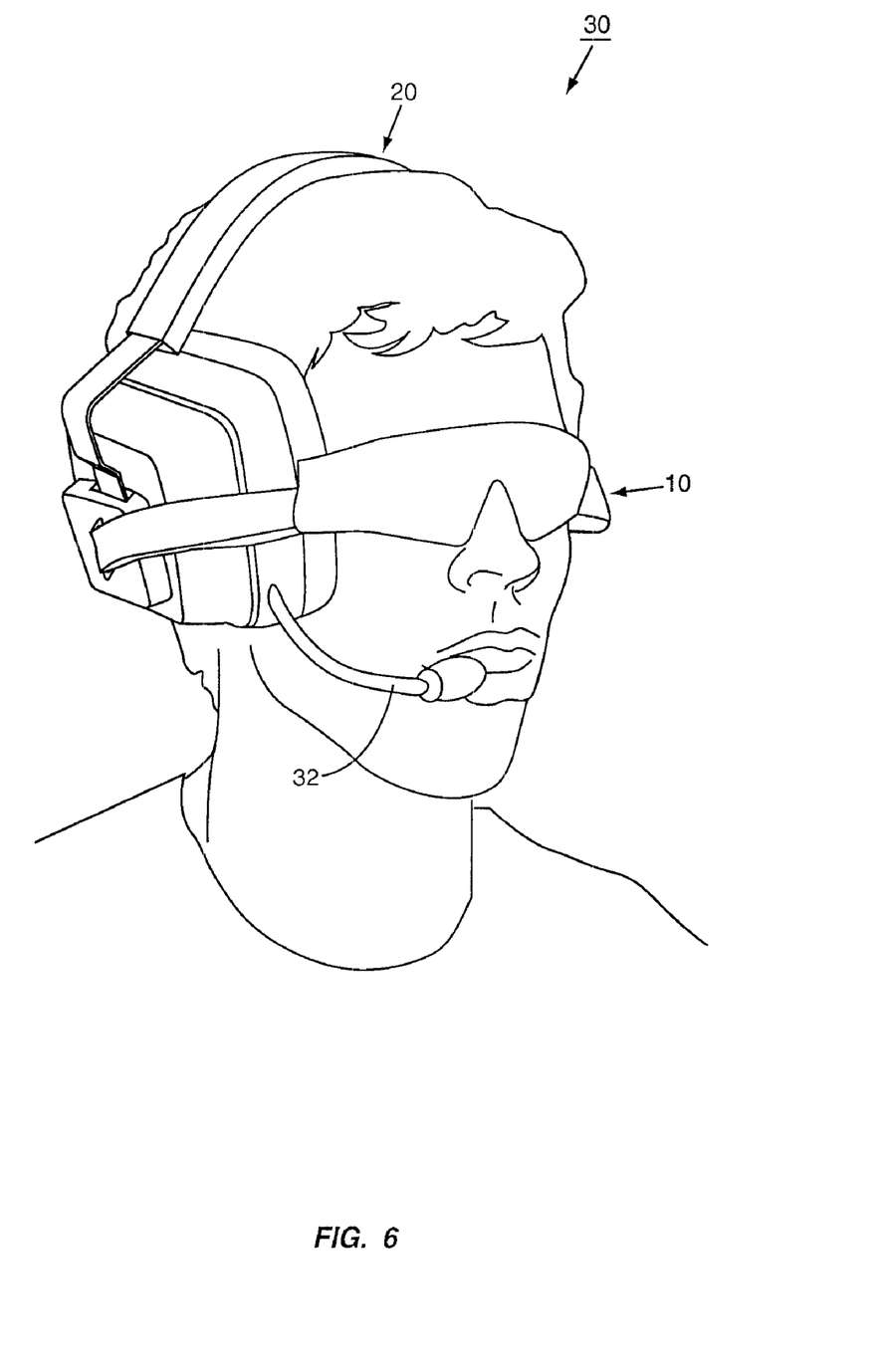
FIG. 6 illustrates the present invention in use by an individual.

A combination 30 of eyewear 10 and headset 20 is shown in FIG. 6. Headset 20 may include microphone 32, such as is commonly used by aviators. From FIG. 6, it is readily apparent that the user may don the headset 20 and easily selectively add or remove the eyewear 10 as needed or desired without having to remove the headset 20. This is particularly advantageous for aviators who may need to don sunglasses when they break cloud cover or construction workers who may need to don periodically protective eyewear. Further, it is not necessary to pierce the seal 24 to don or remove the eyewear 10 thereby preserving the integrity of the sound protection afforded by the headset 20. Likewise, other professions or users may benefit from the present invention.

It should be appreciated that the present invention is easily retrofit onto existing headsets. In particular, the eyewear 10 may be manufactured to accommodate the present invention with a first fastener portion 14 thereon. The second fastener portion 14 may accompany the eyewear 10 along with an adhesive or other securing means through which the complimentary portion of the fastener 14 is secured to the exterior surface 23. For example, if a hook-and-loop fastener is used to secure the eyewear 10 to the headset 20, the eyewear 10 would include a first portion of the hook-and-loop fastener 14 and the other portion of the hook-and-loop fastener 14 would be sold with an adhesive backing and a protective strip. In use, the protective strip would be removed and the adhesive backing applied to the exterior surface 23 of the headset 20 thereby putting the headset 20 in condition for use with the eyewear 10 of the present invention.

The length of the temples 12 may be adjusted as needed or desired to provide a good fit of eyewear 10 for the user.

Figure 7A:
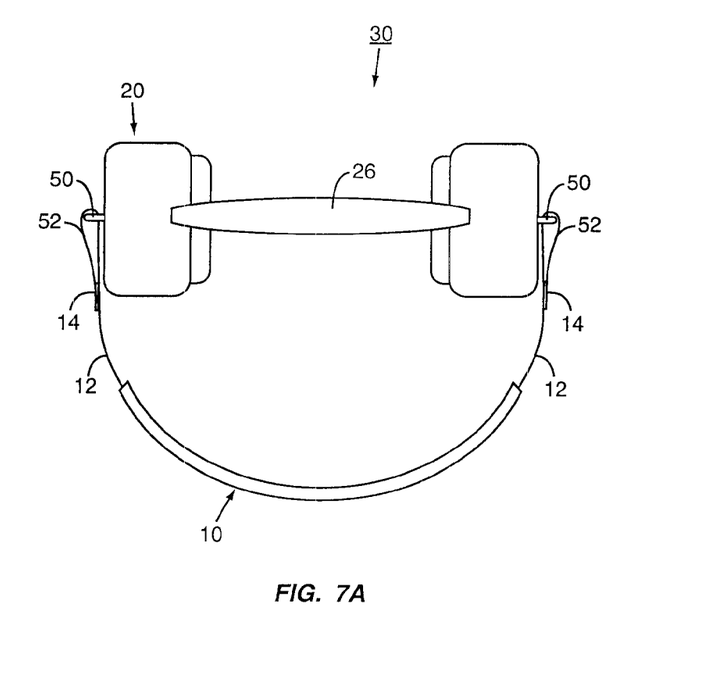
FIGS. 7A & 7B illustrate an alternate embodiment of the temples in conjunction with the combination of the present invention.
Figure 7B:
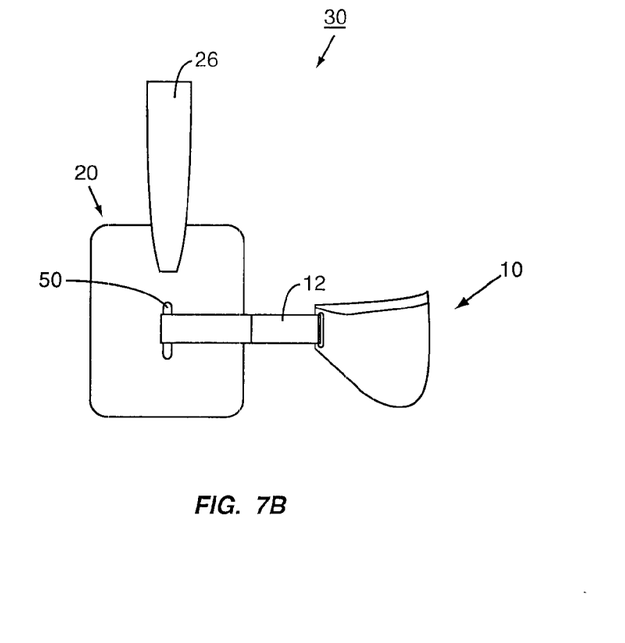

An alternate embodiment of temples 12 is illustrated in FIGS. 7A & 7B. In particular, instead of positioning a portion of the fastener 14 on the headset 20, as illustrated in the previous embodiments, this alternate embodiment requires that headset 20 include a side member 50, through which the temple 12 may be threaded and then folded back on itself thereby forming a loop 52 such that the fastener 14 may be used to fasten to temple 12 to itself. It should be appreciated that the loop 52 may be formed by folding the temple 12 inwardly (shown) or outwardly (not shown). However, folding the temple 12 inwardly may be easier for practical purposes. Further the type of fastener 14 may similarly be varied amongst the many equivalent fasteners previously discussed.

Figure 8:
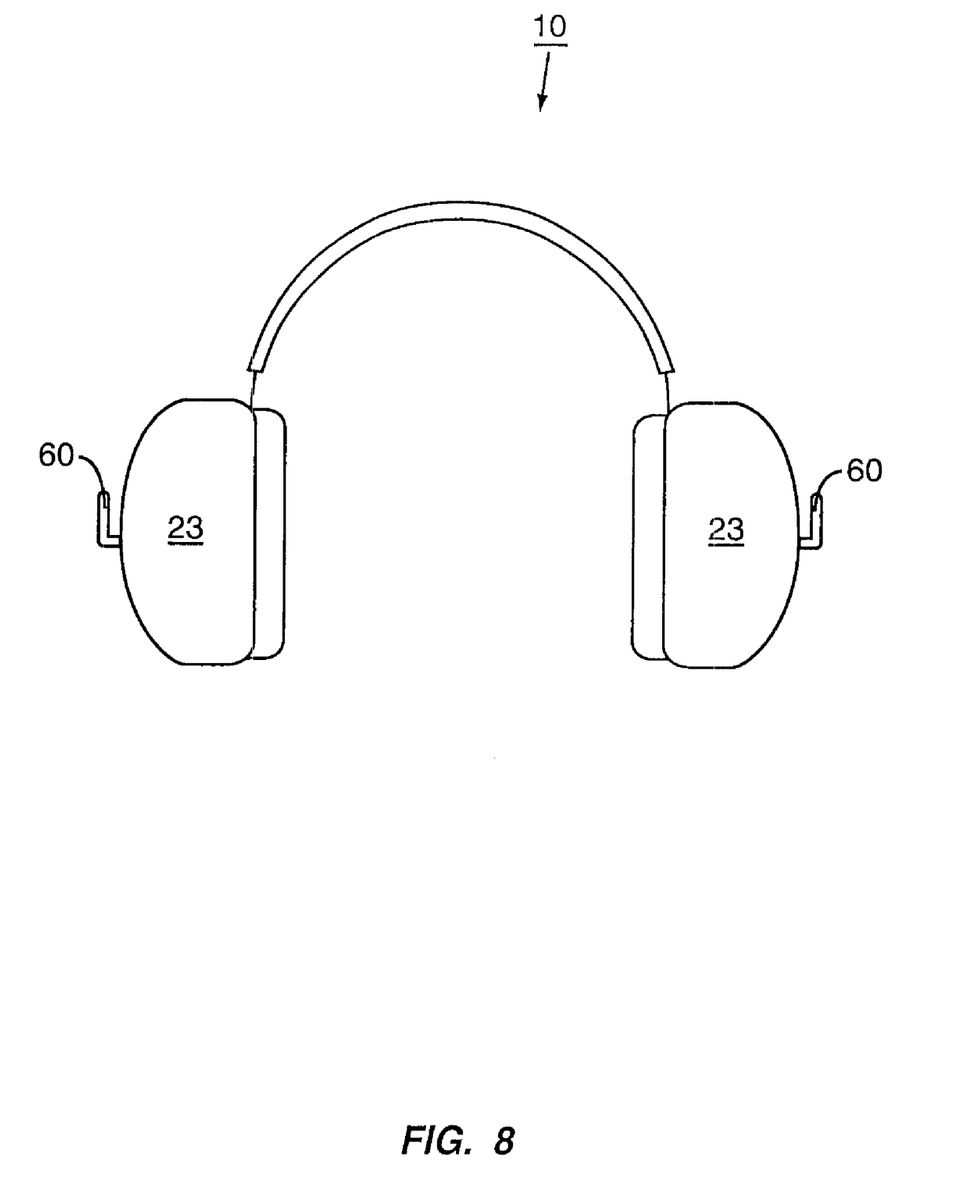
FIG. 8 illustrates another alternate embodiment of the fastener.

Another alternate embodiment is illustrated in FIG. 8, wherein the headset 20 includes vertical posts 60 over which a loop in temple 12 may be slipped. Posts 60 may be generally L-shaped, or merely slanted away from the exterior surface 23 of the headset 20. While described as vertical, posts 60 may alternatively be at almost any angle as long as a loop may be slipped thereover and eyewear 10 secured to the headset 20.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. In combination, a headset and eyewear, said headset comprising:

an arch positioned between first and second muffs and adapted to keep said first and second muffs positioned over the ears of a user; and a first portion of a fastener, and said eyewear comprising flexible temples adapted to be selectively secured by a second portion of the fastener to the headset, wherein said fastener comprises a hook-and-loop fastener.

2. The combination of claim 1, wherein said first and second muffs comprise sound protective earmuffs.

3. The combination of claim 1, wherein said first and second muffs comprises headphones.

4. The combination of claim 1, wherein said eyewear are sunglasses.

5. A method of utilizing eyewear, comprising: positioning protective earmuffs over the ears of a user; and selectively attaching eyewear to said protective earmuffs with a hook-and-loop fastener.

6. The method of claim 5 wherein selectively attaching eyewear comprises attaching sunglasses to said protective earmuffs.

7. The method of claim 5 wherein selectively attaching eyewear comprises attaching an IFR hood to said protective earmuffs.

8. The method of claim 5 further comprising removing said eyewear without removing said protective earmuffs.

9. A protective device comprising:

a) a headset for protecting a user's hearing, said headset having first and second muffs each having a protective seal that extends around the user's ears;

b) eyewear having lenses sized for protecting the user's eyes, said eyewear further having flexible temples, said temples having a first end fixedly attached to said eyewear and a second end for connecting with said headset; and c) fasteners for connecting said eyewear to said headset, said fasteners including a first member attached to said headset and a second complimentary member attached to said temple second end, said first and second members being complimentary to adhere positively to one another in a fastened position.

10. The device of claim 9, wherein said fasteners are sized to provide a positive indication when placed in said fastened position.

11. The device of claim 9 wherein said fasteners comprises posts and said temples are formed into loops for selective securing over said posts.

12. A method of protecting a user comprising the steps of:

a) placing hearing protection over a user's ears;

b) placing eye protection on the user;

c) adhering the eye protection on the user by fastening flexible temples to an outside surface of the hearing protection;

d) wearing both the hearing and eye protection; and e) removing the eye protection from the user by unfastening the flexible temples from the outside of the hearing protection without removing the hearing protection from over the user's ears.

* * * * *